(12) United States Patent
Alves Da Costa Gonçalves et al.

(10) Patent No.: US 11,248,591 B2
(45) Date of Patent: Feb. 15, 2022

(54) CONTRACTIBLE BAND FOR USE IN A WEARABLE GARMENT COMPRISING A SHAPE MEMORY MATERIAL PART

(71) Applicants: CENTITVC-CENTRO DE NANOTECNOLOGIA E MATERIAIS TÉCNICOS,FUNCIONAIS E INTELIGENTES, Vila Nova de Famalicão (PT); UNIVERSIDADE DO MINHO, Braga (PT); IPCA—INSTITUTO POLITÉCNICO DO CÁVADO E AVE, Barcelos (PT)

(72) Inventors: Carlos Diogo Alves Da Costa Gonçalves, Fafe (PT); Ricardo João Ferreira Simões, Alvelos (PT); Alexandre Manuel Teixeira De Barros Ferreira Da Silva, Guimarães (PT); João Manuel De Carvalho Gomes, Braga (PT)

(73) Assignees: IPCA—INSTITUTO POLITÉCNICO DO CÁVADO E AVE, V Frescainha (S Martinho) Barcelos (PT); CENTITVC—CENTRO DE NANOTECNOLOGIA E MATERIAIS TÉCNICOS, FUNCIONAIS E INTELIGENTES, Vila Nova de Famalicão (PT)

( * ) Notice: Subject to any disclaimer, the term of this patent is extended or adjusted under 35 U.S.C. 154(b) by 121 days.

(21) Appl. No.: 16/621,556

(22) PCT Filed: Jun. 11, 2018

(86) PCT No.: PCT/IB2018/054216
§ 371 (c)(1),
(2) Date: Dec. 11, 2019

(87) PCT Pub. No.: WO2018/229635
PCT Pub. Date: Dec. 20, 2018

(65) Prior Publication Data
US 2020/0102940 A1    Apr. 2, 2020

(30) Foreign Application Priority Data

Jun. 11, 2017  (EP) ................................. 17175389
Jun. 12, 2017  (PT) .................................. 110140
Jan. 22, 2018  (EP) ................................. 18152851

(51) Int. Cl.
*A61F 13/08*       (2006.01)
*A61F 13/00*       (2006.01)
(Continued)

(52) U.S. Cl.
CPC .............. *F03G 7/065* (2013.01); *A61F 13/08* (2013.01); *A61F 2013/0028* (2013.01);
(Continued)

(58) Field of Classification Search
CPC ........ A61F 13/08; A61F 13/085; A61F 13/06; A61F 13/062; A61F 5/0111;
(Continued)

(56) References Cited

U.S. PATENT DOCUMENTS 7,382,945 B1 *   6/2008  Sanders .................... G01T 1/20
                                                          385/12
2010/0056966 A1 * 3/2010  Toth ................... A61H 23/0254
                                                          601/134
(Continued)

OTHER PUBLICATIONS

An optical fiber Bragg grating force sensor for monitoring sub-bandage pressure dring compression therapy; Aug. 26, 2013 | vol. 21, No. 17 | DOI:10.1364/OE.21.019799 | Optics Express 19801 (Year: 2013).*

(Continued)

*Primary Examiner* — Ophelia A Hawthorne
(74) *Attorney, Agent, or Firm* — Leason Ellis LLP (57) ABSTRACT

A textile contractible band for use in a wearable garment for applying pressure to a subject body part includes a shape memory material, in particular a shape memory alloy, or (Continued)

shape memory polymer, part and a textile part, said parts being successively coupled to form said contractible band, wherein the shape memory material part has an electrically-contractible shape memory material and a spring arranged to reverse the contraction of the shape memory material, and wherein the textile part has an elastic fabric band and an optical fiber strain sensor arranged to sense the fabric band strain. The sensor can be a lossy optical fiber arranged in meandering layout such that variation of band extension causes variation of transmitted light. The contractual band can be used for lymphedema or venous return.

14 Claims, 3 Drawing Sheets

(51) Int. Cl.
*F03G 7/06* (2006.01)
*A61H 1/00* (2006.01)

(52) U.S. Cl.
CPC ........ *A61H 1/008* (2013.01); *A61H 2201/165* (2013.01); *A61H 2209/00* (2013.01)

(58) Field of Classification Search
CPC . A61F 2013/0028; F03G 7/065; A61H 1/008; A61H 2201/165; A61H 2209/00; A61H 7/001; A61H 2201/5007; A61H 2201/5071; A61H 2201/164; A61H 2201/5002; A61H 2201/5061; A61H 2205/06; A61H 2205/081; A61H 2205/12; A61H 2201/10; A61H 2201/5092; A61H 2205/106; A61H 2201/5058; A61H 2205/065; A61H 2205/108; A61H 2201/0228; A61H 2201/1623; A61H 2201/1654; A61H 2201/1697; A61H 2201/5082; A61H 2205/022; A61H 2205/10; A61H 39/06; A61H 1/0244; A61H 1/0255; A61H 1/0266; A61H 1/0274; A61H 1/0277; A61H 1/0281; A61H 1/0292; A61H 2201/1628; A61H 2201/1652; A61H 2201/5025; A61H 2205/08; A61H 2230/50; A61H 39/002; A61H 3/00; Y10S 128/15
See application file for complete search history.

(56) References Cited

U.S. PATENT DOCUMENTS

| | | |
|---|---|---|
| 2015/0073318 A1 | 3/2015 | Holschuh et al. |
| 2015/0224011 A1 | 8/2015 | Scott et al. |
| 2016/0004032 A1* | 1/2016 | Wiklof .................. G02B 7/181 |
| | | 359/846 |
| 2016/0175179 A1 | 6/2016 | Pamplin et al. |

OTHER PUBLICATIONS

Holschuh, B.; D. Newman, "Two-spring model for active compression textiles with integrated NiTi coil actuators", Smart Materials and Structures, vol. 24, No. 3, 2015, p. 035011.

Li Sheng et al., "The development of TiNi-based negative Poisson's ratio structure using selective laser melting", Acta Materialia, Elsevier, Oxford, GB, vol. 105, Dec. 24, 2015 (Dec. 24, 2015), p. 75-83.

Li Peng, Yan Zhijun, Zhou Kaiming, Zhang Lin, Leng Jinsong, "Monitoring static shape memory polymers using a fiber Bragg grating as a vector-bending sensor", Optical Engineering, vol. 52, No. 1, Jan. 3, 2013 (Jan. 3, 2013), XP002780996.

David Hsiao-Chuan Wang et al., "An optical fiber Bragg grating force sensor for monitoring sub-bandage pressure during compression therapy", Optics Express, vol. 21, No. 17, Aug. 15, 2013 (Aug. 15, 2013), p. 19799.

* cited by examiner

CONTRACTIBLE BAND FOR USE IN A WEARABLE GARMENT COMPRISING A SHAPE MEMORY MATERIAL PART

CROSS-REFERENCE TO RELATED APPLICATIONS

This application is a U.S. National Stage Application under 35 U.S.C. § 371 of International Patent Application No. PCT/IB2018/054216, filed Jun. 11, 2018 which claims priority to European Patent Application No. 18152851.4, filed Jan. 22, 2018, Portugal Patent Application No. 110140, filed Jun. 12, 2017, 2017 and European Patent Application No. 17175389.0, filed Jun. 11, 2017, the contents of which are each hereby incorporated by reference in their respective entireties.

TECHNICAL FIELD

The present disclosure relates to a textile contractible band for use in a wearable garment for applying pressure to a subject body part, comprising a shape memory material, in particular a shape memory alloy, SMA, or shape memory polymer, SMP, part.

BACKGROUND

Compression garments have applications in many fields such as healthcare therapies, sports performance, cosmetic shapewear, and space wear. Clinically, compression stockings are used for the treatment of a variety of conditions, including venous insufficiency, lymphedema, diabetes, and skin burns [1]. Professional and hobbyist athletes wear compression garments to improve performance and increase comfort during training, while cosmetic shapewear compression garments are widely used to adjust body shape. Mechanical Counter Pressure (MCP) suits have also been proposed to create Earth atmospheric pressure in space environments rather than the current suits that use air pressurization to achieve the appropriate applied skin pressures.

Usually compression garments are made of passive elastic textiles that are taut on the skin, or through inflatable bladder systems. The properties of the compressive garments made of passive elastic textiles are a function of material stiffness and garment sizing [2]. Inflatable bladder systems on the other hand have the potential to actively change the applied pressure over time, enabling a massage effect feature [3]. As an example, these systems can be used to mitigate muscle fatigue in the legs, but have the downside of requiring bulky air pumps, which are prone to leaks, hindering usability.

Active materials provide an alternative route to offer variable compression over time. These materials include shape memory alloys (SMAs), shape memory polymers (SMPs), dielectric elastomer actuators (DEAs), piezoelectric and ionic polymer metal composites (IPMCs). As a result, works on active compression garments include active soft orthotic devices based on SMAs, SMPs and DEAs. These are very distinctive materials in terms of composition, performance, and actuation mechanisms (thermal, electric, magnetic). Although they provide a unique set of features, their application into garments has its restrictions. Ferroelectric polymers require bulky magnets to activate, which makes any device built with them bulky and dangerous to wear due to the potentially high magnetic forces. DEAs demand high activation voltages (>1 kV), which require bulky power supplies and at the same time make DEA actuators unsafe to wear [4]. SMPs reveal viscoelastic behaviour and irrecoverable strain effects. SMAs, in comparison with the previous material solutions, offer the advantage of applying cyclical load when stimulated at regular intervals, and at the same time being lightweight and safe to wear [5].

In addition to the actuation element for compression, an integrated active garment requires the ability to sense compression as well, to achieve a complete control loop. One option is to use elongation sensors as a surrogate for the measurement of applied compression. An elongation sensor can be created directly from capacitive and conductive materials [6] [7], or through the use of optical fibres [8]. Studies of the resistive and capacitive properties of several passive elastic textiles revealed that these sensors tend to have hysteresis [6] [9], which can be problematic for feedback control systems. Elongation sensors based on optical fibres embedded in passive elastic fabrics might be an alternative to the pure textile sensors. These optical fibre sensors use light intensity passing through the fibre to sense fabric elongation. Glass optical fibres have the benefit of being flexible, lightweight, small diameter, and pose no threat of electrical shock [10] [11] [8].

These facts are disclosed in order to illustrate the technical problem addressed by the present disclosure.

GENERAL DESCRIPTION

The present disclosure relates to a textile contractible band to use in a wearable garment applying pressure to a subject body part, comprising a shape memory alloy, SMA, part.

In the present disclosure, alternatively to said shape memory alloy, SMA, other shape memory materials may be used such as shape memory polymer, SMP.

In this disclosure, it is presented the design and characterization of a novel active controlled compression band and respective garment that integrates SMA spring actuators and fibre optic strain sensors embedded directly into a passive compression fabric, capable of producing dynamic compression. The aspect of using the actuation sensor system as a closed-loop, independently controllable compression system capable of providing remotely administered and individually tailorable compression treatments, is also included.

The present disclosure relates to a contractible band for use in a wearable garment for applying pressure to a subject body part, comprising a shape memory material part and a textile part, said parts being successively coupled to form said contractible band, wherein the shape memory material part comprises an electrically-contractible shape memory material and a spring arranged to reverse the contraction of the shape memory material, wherein the textile part comprises an elastic fabric band and an optical fibre strain sensor arranged to sense the strain of the fabric band.

The present disclosure relates to a contractible band for use in a wearable garment for applying pressure to a subject body part, comprising a shape memory alloy, SMA, part and a textile part, said parts being successively coupled to form said contractible band,
  wherein the SMA part comprises an electrically-contractible SMA material and a spring arranged to reverse the contraction of the SMA material,
  wherein the textile part comprises a fabric band and an optical fibre strain sensor arranged to sense the strain of the fabric band.

The present disclosure has advantages as the shape memory material and prior art strain/pressure sensors show hysteresis making open-loop control difficult or impossible. Furthermore, prior art contractible bands show unevenness in the applied pressure, making the prior art pressure sensors inexact as these usually measure pressure at the active part which is shown to be non-representative of the overall pressure being applied to the body part. Furthermore, prior art solutions are not able to produce a "pumping" effect which has requirements in terms of contracting speed but also in terms of letting-up speed.

Alternatively to said shape memory material, another electrically- or thermally-contractible active material part may be used, in particular wherein the electrically- or thermally-contractible active material has hysteresis in respect of the electrical or thermal contraction of the resulting contractible band.

Thus, alternatively to said shape memory alloy, SMA, another shape memory material may be used like a shape memory polymer, SMP.

In an embodiment, the SMA material may be contracted at rest, such that, when in use on a subject body part, the SMA material will be stretched.

In an embodiment, the ends of the contractible band now disclosed may be coupled to each other to form a circular band.

In an embodiment, a contractible band assembly comprises two such contractible bands, wherein ends of said two contractible bands are successively coupled lengthwise to each other to form a circular band.

In an embodiment, the contractible band may be contractible by length-wise contraction.

In an embodiment, the shape memory material part and the textile part are lengthwise coupled to form said contractible band. Alternatively, they may be laterally coupled in succession. Depending on the orientation of the shape memory material part and the textile part, the band may contract laterally or lengthwise. Preferably, the direction of contraction of the shape memory material part and the textile part, and the direction of contraction of the band are aligned, because the construction is simpler.

In an embodiment, the SMA part may comprise a heat-resistant fabric wherein the SMA may be fixed to said heat-resistant fabric, for protecting the subject body part from heat generated by the SMA material.

In an embodiment, the SMA material may be directly electrically-contractible by Joule heating.

In an embodiment, the spring arranged to reverse the contraction of the SMA material may be a coil spring or wire spring.

In an embodiment, the electrically-contractible SMA material can be replaced by an SMP (electrically-contractible), DEA (dielectric actuators), IPMC (ionomeric polymer metallic composites), or another thermally- or electrically-contractible material of equivalent active functionality. In particular, the disclosure is particularly effective for thermally- or electrically-contractible materials showing hysteresis when combined with elastic fabrics.

In an embodiment, the optical fibre strain sensor may be a lossy optical fibre and may be arranged in meandering layout such that a variation of the extension of the fabric band causes a variation of the intensity of the light transmitted by said lossy optical fibre; in particular the lossy optical fibre may be arranged in a "S"-shaped layout or in a serpentine-shaped layout.

In an embodiment, the optical fibre strain sensor may be a fibre Bragg grating optical fibre sensor.

In an embodiment, the optical fibre strain sensor may be sewn onto the fabric band.

In an embodiment, the electrically-contractible SMA material may be a wire, thread, cord or a coil.

In an embodiment, the contractible band now disclosed may further comprise an electronic control unit connected to said SMA material and said optical fibre strain sensor, said control unit comprising a digital control input for controlling the pressure applied to the subject body part and said control unit being configured such that a contracting force applied by the contractible band is hysteresis free in respect of said digital control input.

This disclosure also relates to a garment comprising the contractible band now above described, in particular said garment may comprise a plurality of contractible bands.

BRIEF DESCRIPTION OF THE DRAWINGS

The following figures provide preferred embodiments for illustrating the description and should not be seen as limiting the scope of disclosure, where 101 represents phase 1, 102 represents phase 2, 103 represents phase 3, 104 represents the Fabric $L_{F0}$, 105 represents the Fabric $\delta_{Sf}$, 106 represents the $\Delta_{Activation}$, 107 represents the $\Delta X_{System}$, 108 represents the SMA $L_{S0}$, 109 represents the NiBR Spring, 110 represents the SMA $\delta_{Si}$, 111 represents the SMA $\delta_{Sf}$, 112 represents $X_P$, 113 represents $X_A$, 114 represents the SMA and Equilibrium Position Coordinate Axis and 115 represents the Fabric Coordinate Axis, 116 represents NiTi Coil and 117 represents Fabric, 118 represents the Optical Fiber, 119 represents Input Light, 120 represents Output Light, 121 represents the Snap, 122 represents Pliance, and 123 represents a Strain Sensor.

FIG. 1: Schematic representation of an embodiment of: two-dimensional two-spring device (A); three-dimensional device design from front view (B); three-dimensional device design from top view (C).

DETAILED DESCRIPTION

Wearable applications require candidate active materials to: (1) be activated in a safe way to wear during daily activities; (2) be embedded into a textile substrate without adding significant mass or bulkiness; and (3) generate forces in a controlled manner and produce displacements when stimulated (of sufficient magnitude for the chosen application).

Moreover, it is also important that the integrated compression system is wearable, washable, easy to don/doff, comfortable, and produces appropriate circumferential tension. Making the system wearable and washable implies that the main material needs to be a wearable textile with waterproof (or easily removable) sensors and actuators embedded into the textile. The portability of the device requires that the electric power is supplied from batteries. To facilitate the donning/doffing, a circumferential tension close to 0 Pa may be provided when deactivating the compression device. Comfort can be promoted by actively control and limit the amount of pressure applied. Also, a uniform pressure distribution and elimination of pressure hot spots improves the perception of comfort. Moreover, it is important to minimize the number of sensors and actuators to limit bulkiness and energy consumption.

According to these requirements, SMA springs are appropriate actuators. Combining nickel titanium (NiTi) coil actuators and a glass optical fibre elongation sensor into a single garment enables dynamically-generated circumferential tension (and therefore pressure) that can be sensed in real-time. Specifically, when an electrical stimulus is applied to the NiTi coil actuators, they constrict, stretching the remainder of the passive garment and creating circumferential tension on the wearer. As the fabric stretches, so does an embedded glass fibre, creating changes in the optical properties that can be detected and interpreted to estimate garment strain (which then can be correlated to garment counter-pressure).

The system here presented can used SMA coils actuators previously developed by Holschuh et al. [13] or SMA wires. Once in the textile, they can be stimulated via Joule heating using an electric stimulus to enable the phase change and generate the overall SMA length change.

After the electric stimulus is removed, the passive elastic fabric slowly extends to the initial state and is aided by the force generated by the overstretched fabric. Since this can have a long time constant (due to the low restorative forces), a common spring was added in parallel to aid in restoring the SMA to the initial position.

Figure 1A:
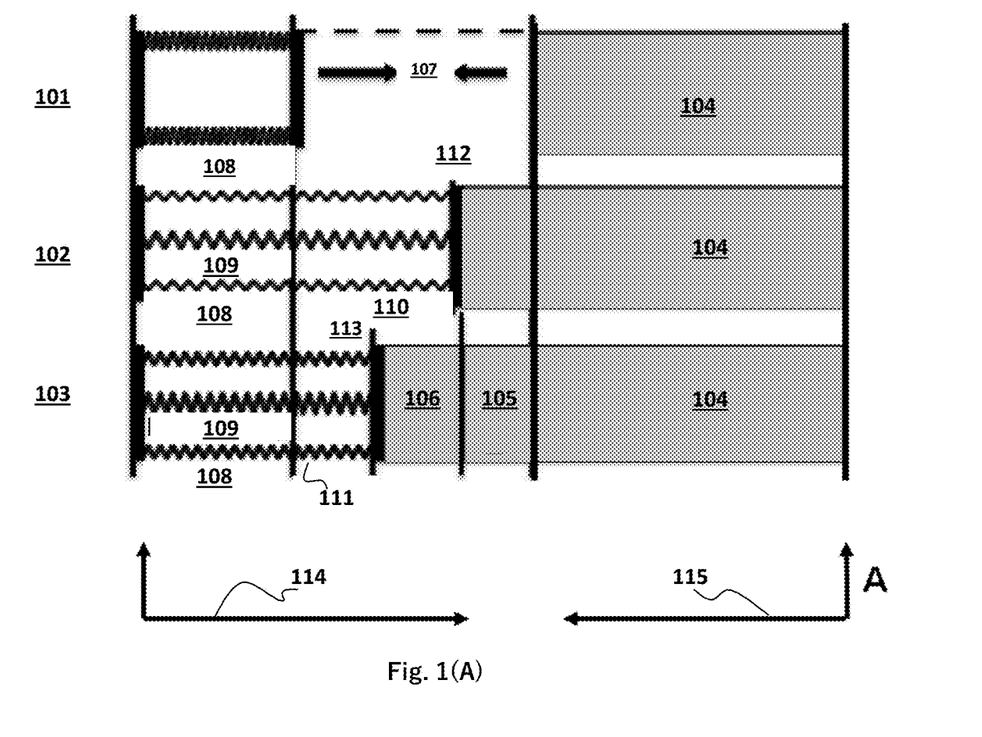

This activation cycle can be divided into three phases (FIG. 1A). In the first phase, the elastic textile and passive spring extend the NiTi coils, causing de-twinning of the crystal structure through the extension of the SMA. In the second phase, the de-twinned SMAs are heated using Joule effect via an applied current [20], which generates a contraction as the austenite phase transformation occurs. In the third and final phase, the SMAs cool, re-entering the twinned martensite phase, which will allow the cycle to be repeated. During the third phase, the common spring aids the SMAs to recover the initial Phase 1 position.

Figure 1B:
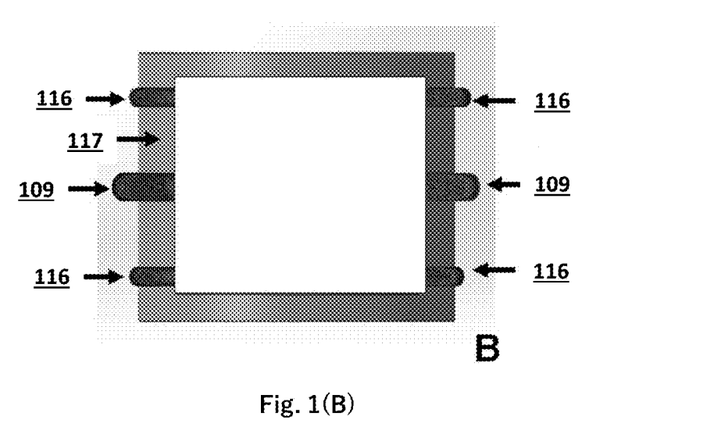

For this device, the SMAs were attached to the elastic fabric using snaps. This design prevented the NiTi actuators from short-circuiting and fixed the actuators in place, preventing structural failure during activation. The snaps were a brass/nickel alloy, which provided electric conductivity in the SMA-snap junction, allowing the electrical stimulus to reach the SMAs. Previous designs found that using one circumferential set of SMA actuators generated unequal circumferential pressures. Here the SMAs were distributed in two sets positioned in two opposite circumferential poles to create a more even circumferential tension distribution (FIG. 1B).

The two-spring model developed by Holschuh et al. [12] for active compression textiles was extended to design the active controlled compression device. For this new model, eleven design variables (Table I) were considered to select the active and passive component properties. The passive and active pressures are a function of the relative unstretched lengths of the conjoined SMA-fabric system compared to the circumferential radius.

TABLE I

Summary of the input/output variables used in the two-spring Model

| Symbol | Value | Unity | Description | Source |
|---|---|---|---|---|
| C | 3 | — | SMA Spring index | * |
| d | 0.31 | mm | SMA wire diameter | ** |
| $G_a$ | 7.5 | GPa | SMA austenite shear modulus | * |
| η | 0.9 | — | SMA Spring packing density | * |
| $L_{s0}$ | 4 | cm | SMA twinned-martensite length | ** |
| $n_a$ | 4 | — | Number of active coils of SMA | ** |
| r | 7.5 | cm | Radius | ** |
| w | 4 | cm | Passive fabric axial width | ** |
| E | 1.3 | MPa | Passive fabric Young's Modulus | *** |
| t | 1.4 | mm | Passive fabric material thickness | *** |
| $L_{F0}$ | 31 | cm | Passive fabric unstretched length | *** |
| k | 20 | N.m$^{-1}$ | Spring's constant | *** |
| $\Delta X_{System}$ | 12 | cm | Unstretched system closure gap | *** |
| $\Delta X_{Activation}$ | 7 | cm | SMA stroke during activation | *** |
| $P_P$ | 0 | Pa | Passive pressure | *** |
| $P_{Active-SMA}$ | 5.5 | kPa | Active pressure | *** |

* Literature Value;
** Selected Value;
*** Calculated Value.

Figure 1C:
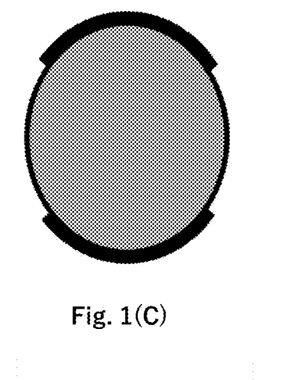

The implementation of the two-spring model assumes an architecture where parallel SMAs (with $L_{S0}$ initial twinned-martensite length) are attached to one end of an elastic fabric strip (with $L_{F0}$ unstretched length). After the fabric and actuators are stretched around a cylindrical object with a radius r, the ends are joined together (Phase 1 on FIG. 1). This will produce a passive equilibrium pressure ($P_P$), which can be calculated using Equation 1:

$$P_P = \left(\frac{Et}{r}\right)\left(\frac{2\pi r - L_{S0}(1 + \varepsilon_{Smax})}{L_{F0}} - 1\right) \quad (1)$$

At this point, an equilibrium position ($X_P$) is reached as a result of the SMAs and textile stretch. A common spring is placed in the middle of the SMAs. The common spring has the same length of the stretched SMAs, which means that it will not influence the passive pressure achieved at passive equilibrium represented at Phase 1 in FIG. 1.

When the SMAs are stimulated by an electric current (Phase 2 on FIG. 1) the temperature will increase, which will contract the actuators and stretch the conjoined elastic fabric and passive spring. The SMAs reach a maximum contraction stroke, the position for which $X_A$ will signify the point where SMA force is perfectly balanced in respect to the elastic force generated by the passive spring-fabric system as it stretches. The NiTi coils stroke length verified during activation is defined as $\Delta X_{Activation}$ ($X_P$–$X_A$).

When the electric current is removed from the SMA actuators, the force from the passive NiBR Spring together with the force of the stretched elastic textile will pull back (i.e., de-twin) the NiTi coils to the equilibrium position represented at Phase 1 in Equation 2 calculates the active pressure ($P_{Active-SMA}$) achieved when the NiTi coils are stimulated:

$$P_{Active-SMA} = \frac{G_A d^2 n_a (Ewt\Delta X_{System} - kL_{F0}\Delta X_{Activation})}{rw(G_A d^2 n_a L_{F0} + Ewt 8C^3 \eta L_{S0})} \quad (2)$$

The common spring makes it necessary to change the active pressure formula developed by Holschuh et al. [12], in order to incorporate the additional force generated by the added NiBR Spring. The SMA stroke during activation ($\Delta X_{Activation}$) it is a calculated parameter that makes easier to present Equation 2. This equation can be straightforwardly derived from the following.

The counter pressure is given by the thin-walled hoop stress equation:

$$P_{Active-SMA} = \frac{F_A}{rw}$$

The active force ($F_A$) is given by the following equation:

$$F_A = \left(\frac{G_A d^2 n_a}{8C^3 \eta L_{S0}}\right)\delta_{Sf}$$

The active displacement ($\delta_{Sf}$) is given by the equilibrium of forces between NiTi coils ($F_{SMA}$), passive elastic fabric ($F_{Fabric}$) and the NiBr spring ($F_{Spring}$):

$$F_{SMA} = k_1 \delta_{Sf}$$

$$F_{Fabric} = -k_2(\delta_{Sf} - \Delta X_{System})$$

$$F_{Spring} = -k\Delta X_{Activation}$$

$$F_{SMA} = F_{Fabric} + F_{Spring}$$

$$k_1 \delta_{Sf} = -k_2(\delta_{Sf} - \Delta X_{System}) - k\Delta X_{Activation}$$

$$\delta_{Sf} = \left(\frac{k_2}{k_1 + k_2}\right)\Delta X_{System} - \left(\frac{k}{k_1 + k_2}\right)\Delta X_{Activation}$$

$$\delta_{Sf} = \left(\frac{Ewt 8C^3 \eta L_{S0}}{G_A d^2 n_a L_{F0} + Ewt 8C^3 \eta L_{S0}}\right)\Delta X_{System} -$$

$$\left(\frac{k8C^3 \eta L_{S0} L_{F0}}{G_A d^2 n_a L_{F0} + Ewt 8C^3 \eta L_{S0}}\right)\left(L_{S0}\varepsilon_{Smax} - \frac{\Delta X_{System} Ewt 8C^3 \eta L_{S0}}{G_A d^2 n_a L_{F0} + Ewt 8C^3 \eta L_{S0}}\right)$$

$$\delta_{Sf} = \left(\frac{Ewt 8C^3 \eta L_{S0}}{G_A d^2 n_a L_{F0} + Ewt 8C^3 \eta L_{S0}}\right)\Delta X_{System} -$$

$$\frac{k8C^3 \eta L_{S0}^2 L_{F0}\varepsilon_{Smax}(G_A d^2 n_a L_{F0} + Ewt 8C^3 \eta L_{S0}) - 64k\Delta X_{System} Ewt L_{F0} C^3 \eta L_{S0}^2}{(G_A d^2 n_a L_{F0} + Ewt 8C^3 \eta L_{S0})^2}$$

$$\delta_{Sf} = \left(\frac{Ewt 8C^3 \eta L_{S0}}{G_A d^2 n_a L_{F0} + Ewt 8C^3 \eta L_{S0}}\right)\Delta X_{System} -$$

$$\frac{8C^3 \eta L_{S0}[L_{F0}L_{S0}k\varepsilon_{Smax}(G_A d^2 n_a L_{F0} + Ewt 8C^3 \eta L_{S0}) - L_{F0}L_{S0}k 8\Delta X_{System} Ewt\eta]}{(G_A d^2 n_a L_{F0} + Ewt 8C^3 \eta L_{S0})^2}$$

$$\delta_{Sf} = (8C^3 \eta L_{S0})\left[\frac{Ewt\Delta X_{System}}{G_A d^2 n_a L_{F0} + Ewt 8C^3 \eta L_{S0}} - \frac{L_{F0}L_{S0}k\varepsilon_{Smax}}{G_A d^2 n_a L_{F0} + Ewt 8C^3 \eta L_{S0}} + \frac{L_{F0}L_{S0}k 8\Delta X_{System} Ewt\eta}{(G_A d^2 n_a L_{F0} + Ewt 8C^3 \eta L_{S0})^2}\right]$$

Replacing active displacement ($\delta_{Sf}$) in the active force ($F_A$) it is possible to achieve the folowing equation:

$$F_A = (G_A d^2 n_a)\left[\frac{Ewt\Delta X_{System}}{G_A d^2 n_a L_{F0} + Ewt 8C^3 \eta L_{S0}} - \frac{L_{F0}L_{S0}k\varepsilon_{Smax}}{G_A d^2 n_a L_{F0} + Ewt 8C^3 \eta L_{S0}} + \frac{L_{F0}L_{S0}k 8\Delta X_{System} Ewt\eta}{(G_A d^2 n_a L_{F0} + Ewt 8C^3 \eta L_{S0})^2}\right]$$

Replacing active force ($F_A$) in the counter pressure formula it is possible to achieve the folowing equation:

$$P_{Active-SMA} = \left(\frac{G_A d^2 n_a}{rw}\right)\left[\frac{Ewt\Delta X_{System}}{G_A d^2 n_a L_{F0} + Ewt 8C^3 \eta L_{S0}} - \frac{L_{F0}L_{S0}k\varepsilon_{Smax}}{G_A d^2 n_a L_{F0} + Ewt 8C^3 \eta L_{S0}} - \frac{L_{F0}L_{S0}k 8\Delta X_{System} Ewt\eta}{(G_A d^2 n_a L_{F0} + Ewt 8C^3 \eta L_{S0})^2}\right]$$

Making:

$$\Delta X_{Activation} = L_{S0}\varepsilon_{Smax} - \frac{L_{S0} 8\Delta X_{System} Ewt\eta}{G_A d^2 n_a L_{F0} + Ewt 8C^3 \eta L_{S0}}$$

Replacing $\Delta X_{Activation}$ on $P_{Active-SMA}$ $$P_{Active-SMA} = \frac{G_A d^2 n_a(Ewt\Delta X_{System} - kL_{F0}\Delta X_{Activation})}{rw(G_A d^2 n_a L_{F0} + Ewt 8C^3 \eta L_{S0})}$$

Figure 2:
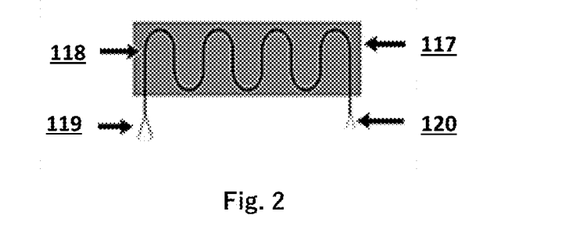
FIG. 2: Schematic representation of an embodiment of the strain sensor made of an optical fibre sewn into an elastic textile (stretch forces applied to the fabric increase the optic fibre curvature, which increase the amount of output light).

Besides the SMA actuators, a strain sensor was developed that measures textile length change. The textile length changes are then related to a circumferential tension. This relationship allowed for real-time monitoring of the applied pressure generated by the active compression device. The elongation sensor, according to an embodiment, was made of a single mode optical fibre (ø=900 μm), sewn into an elastic passive textile (Vicking Lycra 70% cotton/30% polyester) in a double wave shape (FIG. 2). The optical fibre with eleven wave shapes was attached with the fabric unstretched. Increasing the number of waves or decrease the curvature diameter of the waves decrease the fibre optic output light, which decrease the resting sensed voltage at the photodetector. With the described fibre optic configuration the output voltage was 1.5 V after amplification. These eleven wave shapes and curvature diameter allow the sensed voltage to increase up to 1.9 V after amplification when the fabric is stretched. The curvature of the elongation fibre was selected to prevent damaging the sensor while optimizing the resolution. Decreasing the optical fibre wave curvature diameter could damage the optical fibre and limit the amount of light passing through. With this design architecture, it was possible to embed the sensor unobtrusively into an elastic textile.

The fibre optic connectors were coupled with a light emitter and a photo detector. When the SMAs stretch, the light amplitude passing through the fibre increases, and consequently the output voltage coming out of the photodetector also increases. Thus an increment in the difference of voltage depends on the textile elongation ($\Delta l$). The change in voltage can be related to the textile elongation, and thus the applied force, F, was calculated using Young's Modulus as:

$$F = \frac{A \cdot \Delta l}{l_0} E \quad (3)$$

where A is the transversal area of the textile, $\Delta l$ is the elongation of the textile, $l_0$ is the initial length of the textile and E is the Young's Modulus of the textile. The thin-walled hoop stress equation expresses the tension, T, as F per axial width, w:

$$T = \frac{A \cdot \Delta l}{w l_0} E \quad (4)$$

The counter-pressure target, P, is the tension force divided by the radius r as:

$$P = \frac{A \cdot \Delta l}{r w l_0} E \quad (5)$$

Customized hardware and software were developed to operate the elongation sensor. The output voltage from the photodetector was amplified and digitized using the analog to digital converter (ADC) of the microcontroller. The photodetector output voltage is a function of the light level. Functionally, this means that the output voltage remains stable until enough light arrives or leaves the photodetector to change the output voltage to a higher level, which discretizes the photodetector output and consequently discretize the applied pressure measurement too. The digital output voltage value was sent to a computer by Bluetooth. The circuit could be powered by a battery or plugged into a 5 V power supply.

A data acquisition software interface was built in C# to collect the sensor data in real time and save a log file for later analysis.

An ON/OFF control was developed to have a consistent time spent during the compression and relaxation periods across all compression cycles performed for the data analysis. At each 180 s interval, the voltage output of the microcontroller pin was kept high (3.3 V) for 30 s, which triggered the gate of an NPN MOSFET and consequently allowed the current to flow through the SMAs attached between the power supply and the source of the NPN MOSFET. After 180 s the microcontroller pin was set to low (0 V), which disabled the gate of the NPN MOSFET, stopping the current from flowing through the SMAs. When the current was removed, the SMAs cooled, and started to expand with the passive forces of the textile and common spring, decreasing the fabric stretch (and thus, decreasing the sensed pressure). The current on-time was set to 30 s to enable a full state transition and thus maximum contraction. The 180 s between each activation cycle was selected to allow the textile and the NiTi coils to fully recover (i.e., cool and de-twin).

The compression device was characterized to assess the pressure over time, pressure location, and sensor performance. The compression garment was placed around a rigid cylinder (r=75 mm), and ten compression cycles were completed to prove the overtime repeatability of the system. All cycles were powered with the same power settings (2.1 V, 0.3 A, 0.6 W). These power settings were the lowest power necessary to activate the actuators.

To measure the pressure generated by the prototype garment, a Novel Pliance pressure sensor (Novel Electronics, Inc., Munich, Germany) was placed between the garment and the rigid cylinder. A custom S2075 Pliance pressure sensor mat was used (15.24 cm×15.40 cm sensor with 256 sensing sites organized into a 16×16 matrix). The Novel Pliance has the limitation of only sensing pressures above 3.3 kPa. The regions below the operating range were set to 0 Pa. With this pressure sensor, it was possible to directly compare the output of the elongation sensor to the pressure generated on the underlying cylinder, and to measure the pressure generated by the prototype system as a function of both spatial position and time.

Figure 3:
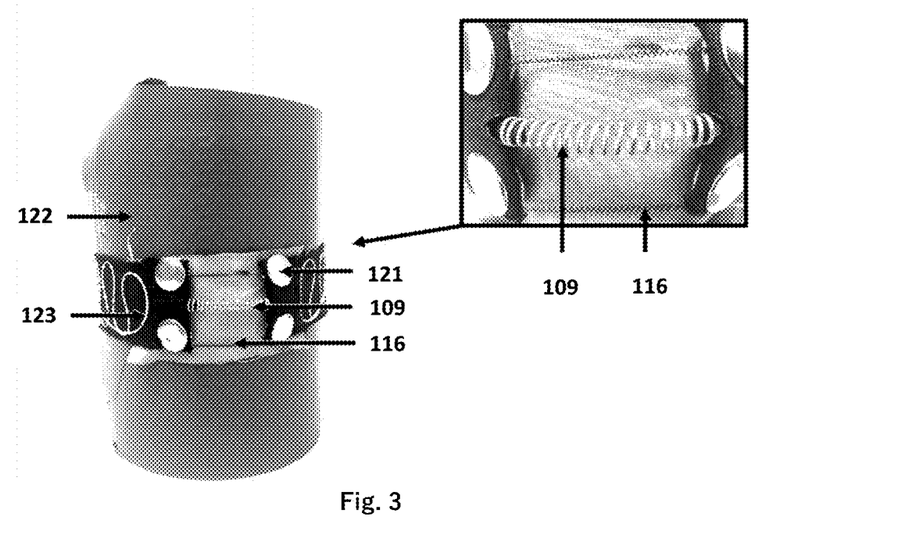
FIG. 3: Photographic representation of an embodiment of active compression fabric setup.

During the experiment, the active controlled compression device was placed in the middle of the Novel Pliance pressure system (FIG. 3) for consistency across trials when using the digital mask. The spatial pressure field was captured over the course of two tests.

The Novel Pliance pressure system captured a matrix of 16×16 sensels, transmitting the 256 pressure values to a computer at 1 a frequency of Hz. As the sensor matrix was larger than the active controlled compression device, a digital mask was used to select the desired 4×16 sensel region. This mask represents the Novel Pliance's pressure area that is in contact with the developed and under test compression fabric device.

The textile elongation was converted to the predicted pressure value using Equation 5. Note that the elongation sensor does not provide spatial resolution. The estimated pressure from the elongation sensor was compared to the average of the 4×16 matrix from the Novel Pliance pressure system.

The columns averages of two trials (generating a 4×32 matrix) were used to quantify the distribution of pressure from the peak of the compression cycles.

The repeatability of the compression cycles sensed with both sensors was evaluated with correlation coefficients between them.

The developed model was used to establish a relationship between the initial length of the textile ($L_{F0}$) and the initial NiTi coil length ($L_{S0}$). The passive pressure ($P_P$) was established to be 0 Pa, which makes the device easier to don/doff. With a passive pressure of 0 Pa, Equation 1 becomes:

$$L_{F0} = 2\pi r - L_{S0}(1 + \varepsilon_{Smax}) \quad (6)$$

With Equation 6 it is possible to select the textile initial length, depending on radius of the cylindrical shape and the initial length of the NiTi coils. It is important that the initial length of the textile is higher than the initial length of the NiTi coils, to keep low power settings. The values for the initial lengths for the textile ($L_{F0}$) and NiTi coils ($L_{S0}$) are presented on Table 1.

Figure 4:
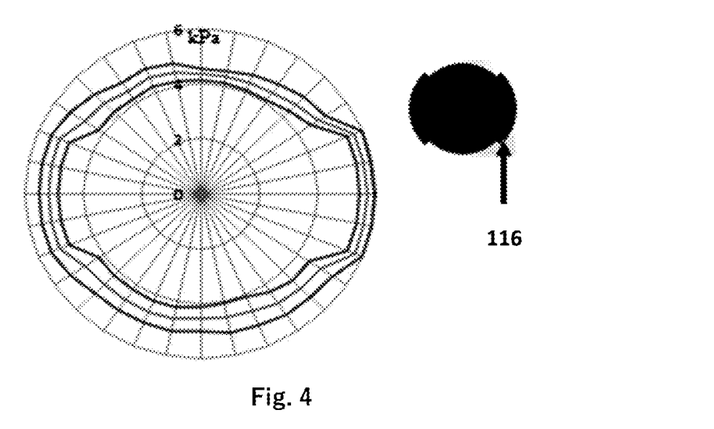
FIG. 4: Schematic representation of results of average Pressure distribution at an external cylinder perimeter wall (centre line) and standard deviation lines (outer and inner lines) of 20 compression cycles (10 in each half of the tube). The spatial pressure field was captured over the course of two tests (as the Novel sensor was not large enough to capture the full circumference in a single test).

The average circumferential peak pressures from the Novel Pliance Sensor across the 20 trials (10 compression cycles in each half of the cylindrical shape) are shown in FIG. 4. The overall mean peak pressure was 4.9 kPa, but ranged between 4.49 and 5.7 kPa based on circumferential location. The peak pressures were found at the NiTi coils location and the lowest pressures were found at the textile location.

Figure 5:
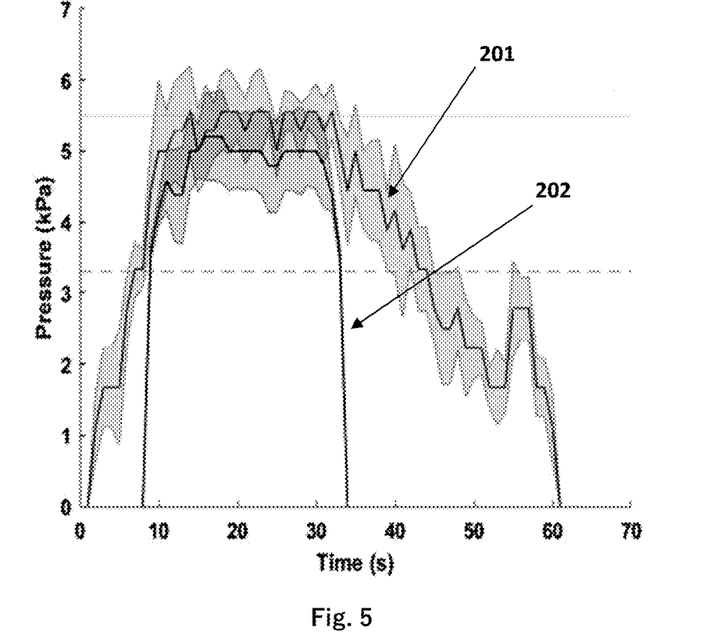
FIG. 5: Schematic representation of results pressure vs. time showing average line and standard deviation of the 10 cycles sensed with the strain sensor (201, centre line with respective deviation). Average line and standard deviation of the 10 compression cycles sensed with the Novel Pliance sensor (202, lower line with respective deviation). Line around 5.5 of value is the maximum predicted active pressure and the line around 3.3 is the Novel Pliance sensors cut-off value.

The time history (FIG. 5) compares the estimated pressures from the elongation sensor with the averaged Novel Pliance sensor data. These data highlight the ramp up time of approximately 8 s for the NiTi coils to complete austenite phase transformation when electrically stimulated. Once in the austenite phase, the maximum pressures observed over the sensed region were 5.5±0.6 kPa. After 30 s the electrical current was removed and the NiTi coils cooled. From the strain sensor, it can be observed that the transition to the martensite state occurred slowly over the next 30 seconds. Here it can also be observed that the pressure values fall below the detectable range of the Novel Pliance sensor.

The average correlation coefficient within the ten compression cycles sensed with the strain sensor was 0.90 with a range of [0.81, 0.95]. The average correlation coefficient within the ten compression cycles sensed with the Novel Pliance sensor was 0.93 with a range of [0.74, 0.99]. The average correlation coefficient between the two measurement methods within trial was 0.92 with a range of [0.86, 0.97].

This disclosure presents the design and characterization of an actively controlled compression garment composed of SMA actuator and real-time fibre optic sensors that were directly embedded into a passive compression fabric. A model of the integrated system was developed and used to select the active and passive garment parameters. The system was developed and applied pressures were measured and characterized. With this model, it was possible to select design parameters using inputs of an applied passive pressure of 0 Pa and a maximum applied active pressure of 5.5 kPa (continuous line on FIG. 5), which is consistent with the acquired values presented in the result section.

The correlation coefficients between the elongation sensor and the Novel Sensor (up to 0.97) show that the strain sensor could be used to estimate the applied pressure in this active controlled compression device. The difference between the maximum pressure sensed with the Novel Pliance Pressure System and the calculated pressure from the elongation sensor can be justified by the blank pressure cells at the 4×16 matrices which poll down the averaged Novel Pliance pressure value.

The pressure profile time history detected with the elongation sensor was longer in duration than that from the Novel Pliance sensor. This difference was due to the sensitivity of the Novel Pliance sensors (cut-off below 3.3 kPa; dashed line on FIG. 5).

The pressure distribution along the perimeter of the cylinder was non-uniform with a maximum pressure value of 5.6 kPa at the NiTi coils and a minimum pressure value of 4.6 kPa at the textile. The current design improved on previously observed non-uniformity. The non-uniformity may stem from the friction of the cylindrical shape and the Novel Pliance Pressure System together with the force of the elastic textile and the SMA make the textile elongation uneven. This uneven textile elongation explains not only the difference between the maximum pressure values sensed with the Novel Pliance Pressure System and the calculated pressure, but also the peaks shown on the calculated pressure slope of the elongation sensor.

The circumferential pressure distribution (FIG. 4) showed higher-pressure values where the NiTi coils were placed. Once again, the friction coefficient of the tube and the Novel Pliance Pressure System together with the force of the elastic textile and the NiBR spring make the textile elongation uneven, which can justify the irregular pressure around the tube.

The Novel Pliance cut-off value below 3.3 kPa affected the ability to estimate the time constants associated with the heating and cooling of the actuators. Another limitation of the Novel Pliance was the sensor mat length as it was shorter than the tube perimeter. Here two cycles were performed to complete a test run for measuring the pressure around the entire perimeter. A limitation in the strain sensors was the lack of spatial resolution. However it was possible to show a correlation between the elongation sensor and the averaged Novel Pliance sensor and the strain sensor.

The disclosure shows that it is possible to embed sensors and actuators into elastic fabrics; making it possible to sense and change applied pressure. The designed system makes it possible to apply repeatable compression cycles comprised by a compression stage and a relaxation stage, repeated sequentially. A new model was derived, making it possible to predict the maximum applied pressure by the developed device. In this disclosure it is also shown how it is possible to use a light strain sensor to measure applied pressure.

An application uses the developed technology to mimic a hand-made massage. This way it is possible to target healthcare treatments for diseases such as lymphedema or venous return.

Figure 6:
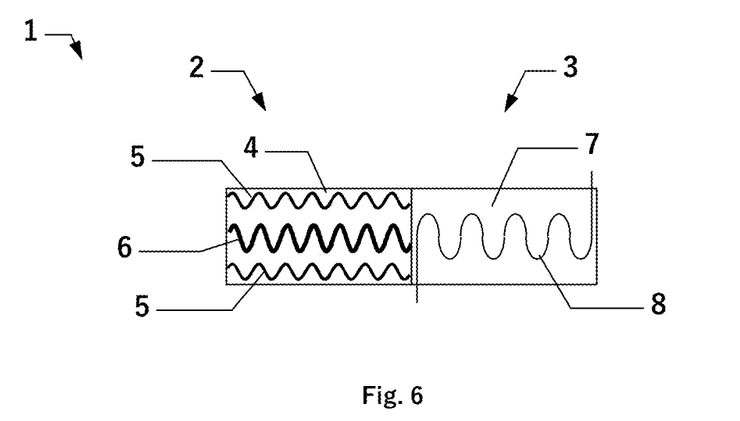
FIG. 6: Schematic representation of an embodiment of a contractible band according to the disclosure.

FIG. 6 shows a schematic representation of an embodiment of a contractible band according to the disclosure, wherein (1) represents a contractible band for use in a wearable garment for applying pressure to a subject body part, (2) represents a SMA part of the contractible band, (3) represents textile part of the contractible band, (4) represents an optional heat-resistant material, (5) represents electrically-contractible SMA material, (6) represents spring, (7) represents a fabric band, (8) represents an optical fibre strain sensor.

The term "comprising" whenever used in this document is intended to indicate the presence of stated features, integers, steps, components, but not to preclude the presence or addition of one or more other features, integers, steps, components or groups thereof. The disclosure should not be seen in any way restricted to the embodiments described and a person with ordinary skill in the art will foresee many possibilities to modifications thereof. The above described embodiments are combinable. The following claims further set out particular embodiments of the disclosure.

REFERENCES

1. Brennan, M. J. and L. T. Miller, Overview of treatment options and review of the current role and use of compression garments, intermittent pumps, and exercise in the management of lymphedema. Cancer, 1998. 83(S12B): p. 2821-2827.
2. Tanaka, K., et al., Mobility of the elastic counterpressure space suit glove. Aviation, space, and environmental medicine, 2009. 80(10): p. 890-893.
3. Figueroa, J. J., et al., Effects of patient-controlled abdominal compression on standing systolic blood pressure in adults with orthostatic hypotension. Archives of physical medicine and rehabilitation, 2015. 96(3): p. 505-510.
4. Plante, J.-S. and S. Dubowsky. On the nature of dielectric elastomer actuators and its implications for their design. in Smart Structures and Materials. 2006. International Society for Optics and Photonics.
5. Abel, J., J. Luntz, and D. Brei, A two-dimensional analytical model and experimental validation of garter stitch knitted shape memory alloy actuator architecture. Smart Materials and Structures, 2012. 21(8): p. 085011.
6. Choong, C. L., et al., Highly stretchable resistive pressure sensors using a conductive elastomeric composite on a micropyramid array. Advanced Materials, 2014. 26(21): p. 3451-3458.
7. Sawhney, A., et al. Piezoresistive sensors on textiles by inkjet printing and electroless plating. in MRS Proceedings. 2006. Cambridge Univ Press.
8. Grattan, L. and B. Meggitt, Optical fibre sensor technology: advanced applications-Bragg gratings and distributed sensors. 2013: Springer Science & Business Media.
9. Yi, W., Flexible Fabric Strain Sensors. Handbook of Smart Textiles, 2015: p. 293-316.
10. Dennison, C. R. and P. M. Wild, Enhanced sensitivity of an in-fibre Bragg grating pressure sensor achieved through fibre diameter reduction. Measurement Science and Technology, 2008. 19(12): p. 125301.
11. Yeh, C., Handbook of fibre optics: theory and applications. 2013: Academic Press.
12. Holschuh, B. and D. Newman, Two-spring model for active compression textiles with integrated NiTi coil actuators. Smart Materials and Structures, 2015. 24(3): p. 035011.
13. Sergueeva, A., et al., Structure and properties of amorphous and nanocrystalline NiTi prepared by severe plastic deformation and annealing. Materials Science and Engineering: A, 2003. 339(1): p. 159-165.

The invention claimed is:

1. A contractible band for use in a wearable garment in order to apply pressure to a subject body part, comprising:
a shape memory material part and a textile part, said parts being successively coupled to form said contractible band,
wherein the shape memory material part comprises an electrically-contractible shape memory material and a spring arranged to reverse the contraction of the shape memory material,
wherein the textile part comprises an elastic fabric band and an optical fibre strain sensor arranged to sense the strain of the fabric band,
wherein said optical fibre strain sensor comprises a lossy optical fibre arranged in a meandering layout within the textile part and wherein a variation of extension of the fabric band causes a variation of intensity of light transmitted by said lossy optical fibre.

2. The contractible band according to claim 1, wherein the shape memory material part is contracted at rest, such that, when in use on a subject body part, the shape memory material part will be stretched.

3. The contractible band according to claim 1, further comprising an electronic control unit connected to said shape memory material and said optical fibre strain sensor, said control unit having a digital control input arranged in a closed-loop in order to control the pressure applied to the subject body part and said control unit being configured such that a contracting force applied by the contractible band is hysteresis free in respect of said digital control input.

4. The contractible band according to claim 1, wherein the shape memory material part and the textile part are lengthwise successively coupled to form said contractible band.

5. The contractible band according to claim 1, wherein the band is contractible by length-wise contraction.

6. The contractible band according to claim 1, wherein ends of the contractible band are coupled to each other to form a circular band.

7. The contractible band according to claim 1, wherein the shape memory material is a shape memory alloy or a shape memory polymer.

8. The contractible band according to claim 1, wherein the shape memory material part comprises a heat-resistant fabric wherein the shape memory material part is fixed to said heat-resistant fabric to protect the subject body part from heat generated by the shape memory material part.

9. The contractible band according to claim 1, wherein the shape memory material is directly electrically-contractible.

10. The contractible band according to claim 1, wherein the shape memory material is directly electrically-contractible by Joule heating.

11. The contractible band according to claim 1, wherein the spring is a coil spring or a wire.

12. The contractible band according to claim 1, wherein the lossy optical fibre is arranged in a "S"-shaped layout or in a serpentine-shaped layout.

13. The contractible band according to claim 1, wherein the electrically-contractible shape memory material is a wire, thread, cord or a coil.

14. A garment comprising one or more contractible bands according to claim 1.

* * * * *